United States Patent [19]
Iijima

[11] Patent Number: 6,053,867
[45] Date of Patent: Apr. 25, 2000

[54] NONCONTACT TONOMETER FOR MEASURING INTRAOCULAR PRESSURE

[75] Inventor: Hiroshi Iijima, Tokyo, Japan

[73] Assignee: Kabushiki Kaisha Topcon, Tokyo, Japan

[21] Appl. No.: 09/371,428

[22] Filed: Aug. 10, 1999

[30] Foreign Application Priority Data

Aug. 19, 1998 [JP] Japan .................................. 10-232826

[51] Int. Cl.$^7$ ........................................................ A61B 3/00
[52] U.S. Cl. ........................................................ 600/399
[58] Field of Search ................................... 600/398, 399, 600/400, 401, 402; 351/212, 221

[56] References Cited

U.S. PATENT DOCUMENTS

5,474,066 12/1995 Grolman ................................. 600/398

*Primary Examiner*—George Manuel
*Attorney, Agent, or Firm*—Chapman and Cutler

[57] ABSTRACT

A noncontact tonometer has a control circuit which actuates a puffing means to apply an air pulse through a puffing nozzle to the cornea of a subject's eye only when it is found from alignment positional information provided by an XY-alignment detecting circuit that the position of an intraocular pressure measuring unit relative to the cornea is in a predetermined range narrower than and in an allowable alignment range when the alignment of the intraocular pressure measuring unit is readjusted after the measurement of the thickness of a specific section of the cornea.

4 Claims, 9 Drawing Sheets

FIG. 11

NONCONTACT TONOMETER FOR MEASURING INTRAOCULAR PRESSURE

BACKGROUND OF THE INVENTION

1. Field of the Invention

The present invention relates to a noncontact tonometer for measuring the intraocular pressure of a subject's eye.

2. Description of the Related Art

A previously proposed noncontact tonometer measures the corneal thickness of the eye after being aligned with the eye, flattens a section of the cornea by applying an air pulse to the cornea by a puffing means, determines the intraocular pressure on the basis of the pressure of the air pulse applied to the cornea, and corrects the measured intraocular pressure on the basis of the measured corneal thickness.

The corneal thickness is not uniform over the entire cornea and different sections of the cornea have different corneal thicknesses, respectively. Since the air pulse is applied to the cornea a little time after the measurement of the corneal thickness, it is possible that a section of the cornea to which the air pulse is applied differs greatly from a section of the same where the corneal thickness is measured due to a small involuntary movement of the eye during the interval between a puffing operation for applying an air pulse to the eye and a corneal thickness measuring operation for measuring corneal thickness. In such a case, incorrect data on the intraocular pressure will be obtained if the measured intraocular pressure is corrected by the measured corneal thickness.

SUMMARY OF THE INVENTION

Accordingly, it is an object of the present invention to provide a noncontact tonometer capable of applying an air pulse to a section of the cornea substantially coinciding with a section of the cornea where the corneal thickness is measured and of determining the intraocular pressure of the eye in a high accuracy.

According to a first aspect of the present invention, a noncontact tonometer includes a position detecting means, a storage means, and a comparing means for comparing information provided by the position detecting means and information provided by the storage means after the measurement of corneal thickness, in which a decision is made on the basis of information provided by the comparing means as to whether or not intraocular pressure measurement is to be executed following corneal thickness measurement, and a puffing operation is controlled.

An air pulse can be applied to a section of the cornea substantially coinciding with a section of the cornea where the corneal thickness is measured to achieve precision intraocular pressure measurement.

According to the second aspect of the present invention, the control means is not executed if it is known from the information provided by the comparing means that the section of the cornea to which an air pulse is applied is dislocated from a section of the cornea where corneal thickness is measured by a distance exceeding a predetermined value, and corneal thickness measurement is executed again.

According to a third aspect of the present invention, the noncontact tonometer corrects the measured intraocular pressure on the basis of measured and calculated corneal thickness.

According to a fourth aspect of the present invention, the noncontact tonometer further includes an informing means for informing the examiner of the calculated corneal thickness, the intraocular pressure or the corrected intraocular pressure.

BRIEF DESCRIPTION OF THE DRAWINGS

The above and other objects, features and advantages of the present invention will become more apparent form the following description taken in connection with the accompanying drawings, in which.

DESCRIPTION OF THE PREFERRED EMBODIMENTS

A noncontact tonometer in a preferred embodiment according to the present invention will be described with reference to the accompanying drawings.

Figure 1:
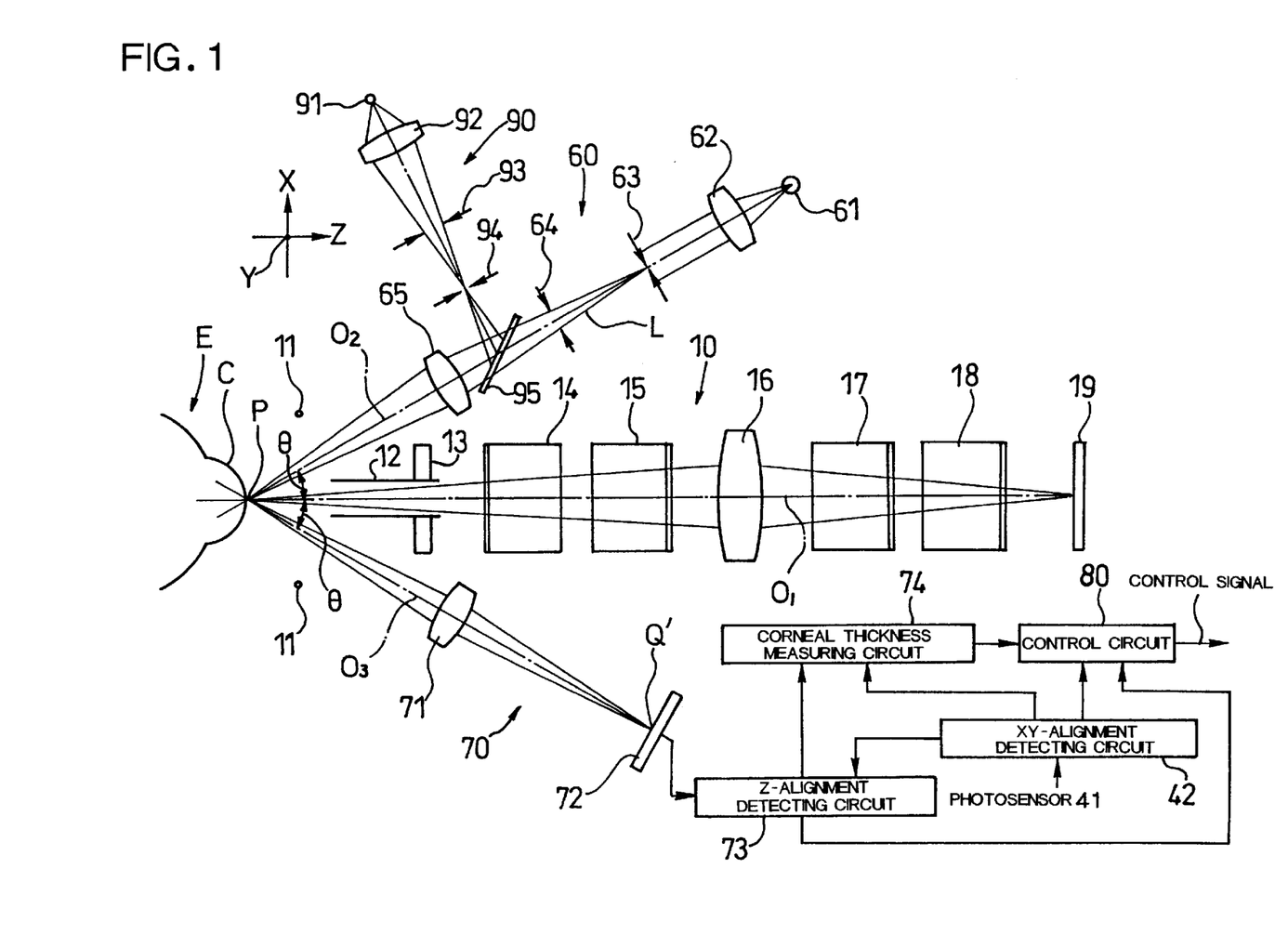
FIG. 1 is a diagrammatic view of an optical system included in a noncontact tonometer in a preferred embodiment according to the present invention.
Figure 2:
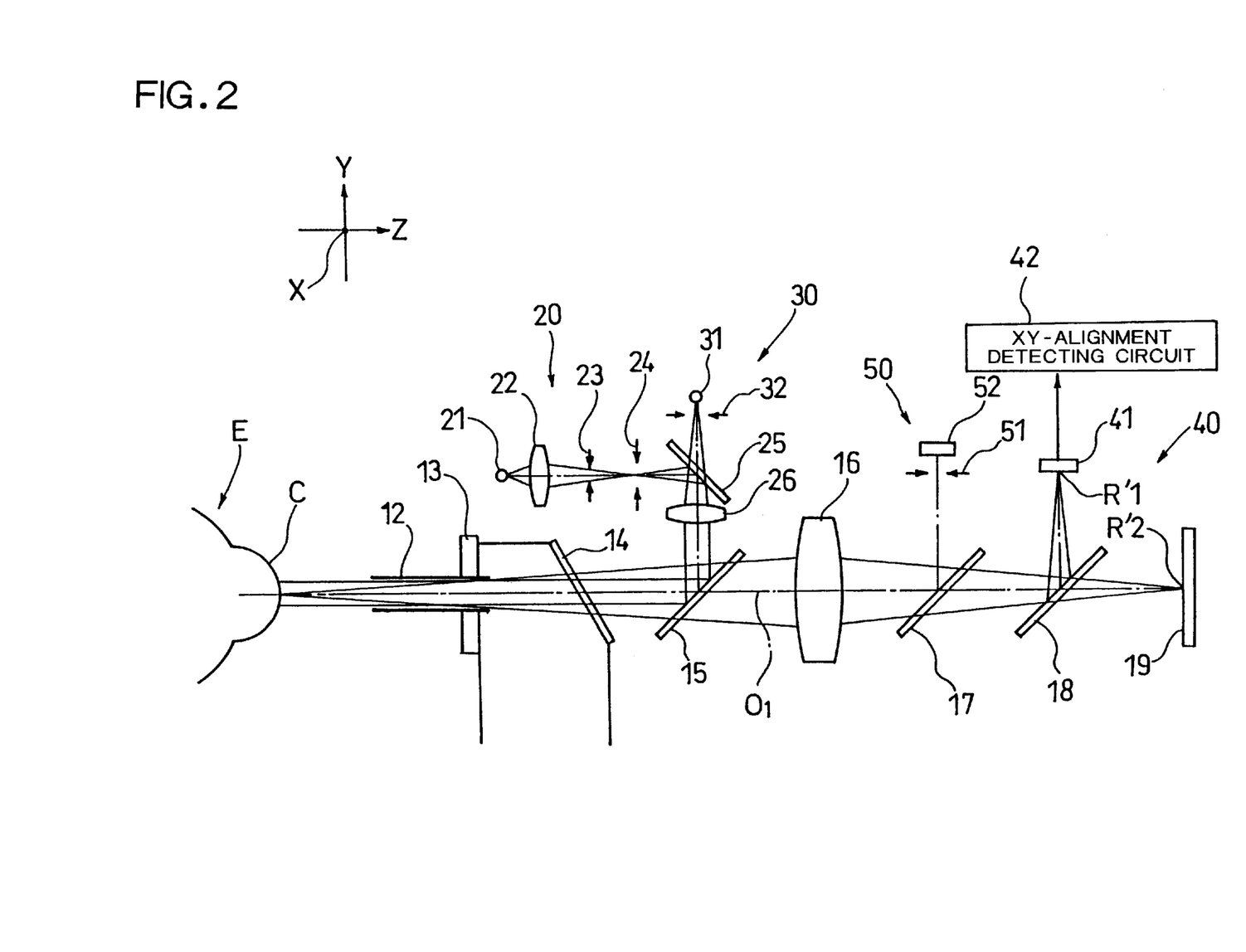
FIG. 2 is a diagrammatic view of the optical system shown in FIG. 1.
Figure 7:
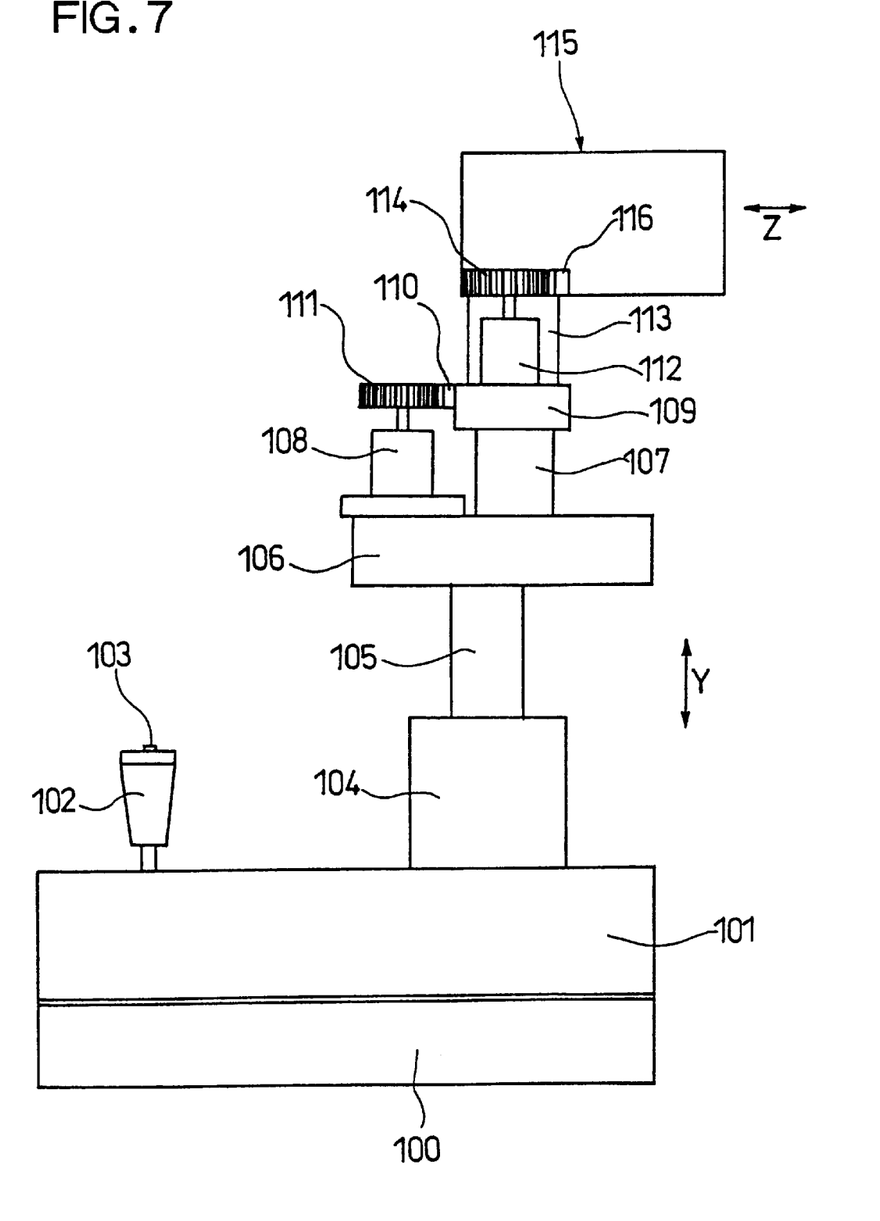
FIG. 7 is a schematic side elevation of the noncontact tonometer shown in FIG. 1.

FIGS. 1 and 2 show an optical system included in the noncontact tonometer in a preferred embodiment according to the present invention. The optical system of the noncontact tonometer is formed in an intraocular pressure measuring unit 115 (FIG. 7).

Referring to FIGS. 1 and 2, there are shown an anterior segment observation optical system 10 for observing the anterior segment of a subject's eye E, an XY-alignment index projecting optical system 20 for projecting an index light beam on the cornea C of the eye E (hereinafter referred to simply as "cornea") from the front for detecting alignments in the X- and Y-directions and detecting corneal deformation. A fixation target projecting optical system 30 for projecting a fixation target on the eye E, an XY-alignment detecting optical system 40 which receives an XY-alignment index light beam reflected by the cornea C to determine the positional relation between the intraocular pressure measuring unit 115 and the cornea C with respect to directions along the X- and the Y-direction, a cornea deformation detecting optical system 50 which receives the reflected XY-alignment index light beam reflected from the cornea C and determines the deformation of the cornea C, a slit projecting optical system 60 for projecting a narrow slit index light beam obliquely on the cornea C, an index projecting optical system 90 for projecting, obliquely on the cornea C, an index light beam wider than the slit index light beam projected by the slit light beam projecting system 60, and a light receiving optical system 70 for receiving the reflected index light beam and the reflected slit light beam reflected from the cornea C. The light receiving optical system 70 has an optical axis $O_3$ extending at an angle θ to the optical axis $O_1$ of the anterior segment observation optical system 10.

The anterior segment observation optical system 10 has a plurality of illuminating light sources 11 disposed on the right and the left side of the eye E to illuminate the eye E directly, a puffing nozzle 12, an anterior segment glass plate 13, a chamber glass plate 14, a semitransparent mirror 15, an objective 16, semitransparent mirrors 17 and 18 and a CCD camera 19.

Light emitted by the illuminating light sources 11 and reflected from the eye E travels through the puffing nozzle 12, the anterior segment glass plate 13, the chamber glass plate 14, the semitransparent mirror 15, the objective 16, and the semitransparent mirrors 17 and 18, and falls on the CCD camera 19. The objective 16 forms an image of the anterior segment of the eye E on the CCD sensor of the CCD camera 19. A puffing means, not shown, applies an air pulse through the puffing nozzle 12 to the eye E. The puffing nozzle 12, the puffing means, and the cornea deformation detecting optical system 50 form a tonometric unit.

The XY-alignment index projecting optical system 20 has an XY-alignment light source 21 which emits infrared rays, a condenser lens 22, an aperture stop 23, a pinhole plate 24, a dichroic mirror 25, a projection lens 26 disposed on an optical path with its focal point coincided with the pinhole plate 24, the semitransparent mirror 15, the chamber glass plate 14 and the puffing nozzle 12.

Figure 3:
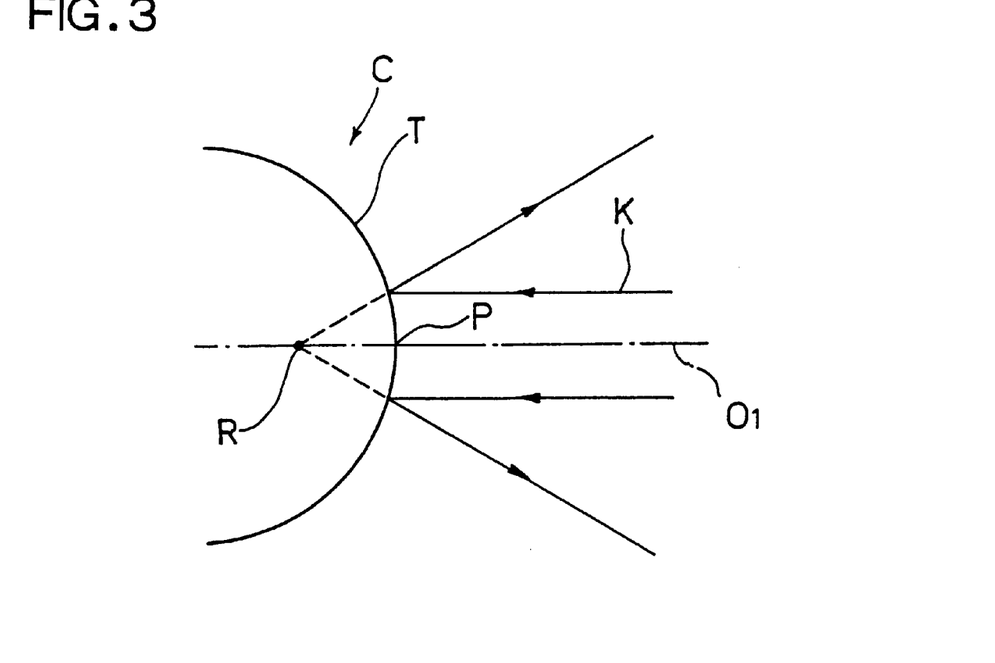
FIG. 3 is a diagrammatic view of assistance in explaining the reflection of an alignment light beam projected along the optical axis of the cornea on the cornea by the noncontact tonometer shown in FIG. 1.

Infrared rays emitted by the XY-alignment light source 21 are gathered by the condenser lens 22, travel through the aperture stop 23 and a pinhole formed in the pinhole plate 24, are reflected by the dichroic mirror 25, are collimated by the projection lens 26 in an infrared beam, and the infrared beam is reflected by the semitransparent mirror 15, travels through the chamber glass plate 14 and the puffing nozzle 12, and forms an XY-alignment index light beam K as sown in FIG. 3. As shown in FIG. 3, the XY-alignment index light beam K is reflected at the surface T of the cornea C so as to form a bright spot image R at an intermediate point on the optical axis $O_1$ between the vertex P of the cornea C and the center of curvature of the cornea C. The aperture stop 23 and the vertex P of the cornea C are in a conjugate relationship with respect to the projection lens 26.

The fixation target projecting optical system 30 has a fixation target light source 31 which emits visible light, a pinhole plate 32, the dichroic mirror 25, the projection lens 26, the semitransparent mirror 15, the chamber glass plate 14 and the puffing nozzle 12.

Fixation target light beams emitted by the fixation target light source 31 travel through the pinhole of the pinhole plate 32 and the dichroic mirror 25, are collimated by the projection lens 26 in a fixation targetlight beam, and the fixation target light beam is reflected by the semitransparent mirror 15, travels through the chamber glass plate 14 and the puffing nozzle 12 and falls on the eye E to form a fixation target mark. The subject fixes the eye E to fix the visual line on the fixation target mark.

The XY-alignment detecting optical system 40 has the puffing nozzle 12, the chamber glass plate 14, the semitransparent mirror 15, the objective 16, the semitransparent mirrors 17 and 18, a photosensor 41, and an XY-alignment detecting circuit 42.

The light beam projected on the cornea C by the XY-alignment index projecting optical system 20 and reflected from the surface T of the cornea C travels through the puffing nozzle 12, the chamber glass plate 14 and the semitransparent mirror 15, is gathered by the objective 16. A part of the reflected light beam travels through the semitransparent mirror 17, and then a part of the light beam is reflected by the semitransparent mirror 18, and the light beam reflected by the semitransparent mirror 18 falls in a bright spot image R'1 on the photosensor 41. The photosensor 41 is, for example, a PSD capable of position detection. The XY-alignment detecting circuit (position detecting means) 42 calculates the positional relation with respect to directions along the X-axis and the Y-axis between the intraocular pressure measuring unit 115 and the cornea C by a known means on the basis of the output by the photosensor 41, and gives calculated data to a corneal thickness measuring circuit (corneal thickness measuring means) 74 and a control circuit 80 serving as a comparing means and a control means.

Figure 4:
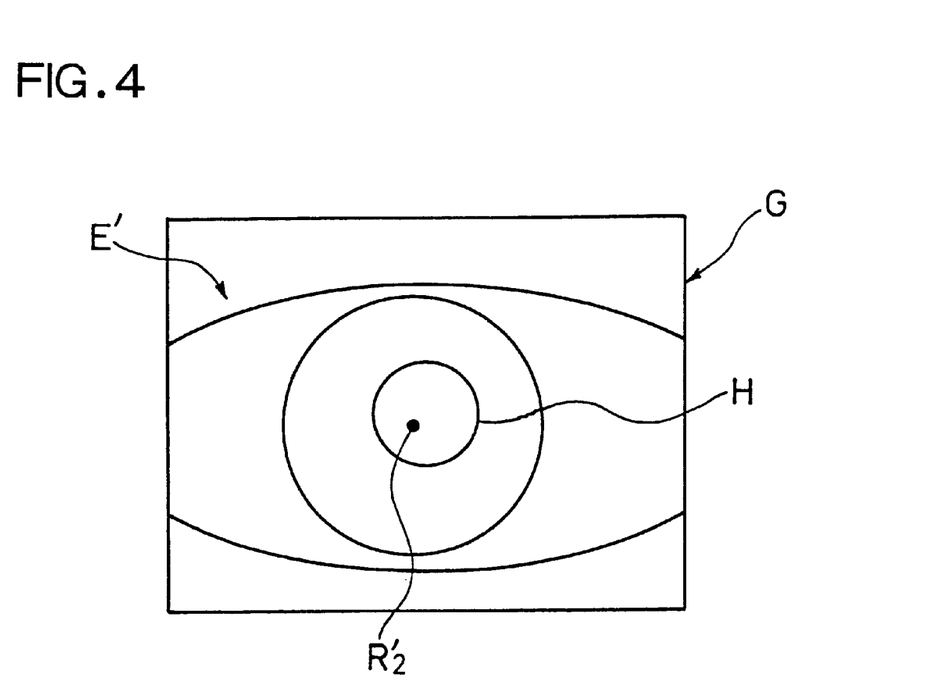
FIG. 4 is a pictorial view of an image of the anterior segment of the eye displayed on the screen of a monitor included in the noncontact tonometer shown in FIG. 1.

The reflected light beam reflected by the cornea C and traveled through the semitransparent mirror 18 forms a bright spot image R'2 on the CCD camera 19. The CCD camera 19 gives an image signal to a monitor. The monitor displays an anterior segment image E', i.e., an image of the anterior segment of the eye E, and the bright spot image R'2 formed by the XY-alignment index light beam as shown in FIG. 4. In FIG. 4, indicated at H is an auxiliary alignment mark produced by an image producing means, not shown.

A part of the reflected light beam reflected by the semitransparent mirror 17 toward the cornea deformation detecting optical system 50 travels through the pinhole of a pinhole plate 51 and falls on a photosensor 52. The photosensor 52 is, for example, a photodiode capable of measuring the intensity of incident light. The cornea deformation detecting optical system 50, and an arithmetic unit, not shown, included in the control circuit 80 form an intraocular pressure measuring means.

The slit projecting optical system 60 has a slit light source 61 which emits infrared rays, a condenser lens 62, a slit plate 63, a rectangular aperture stop 64, a semitransparent mirror 95, and a projection lens 65 disposed with its focal point coincided with the aperture stop 64. The slit projecting optical system 60 has an optical axis $O_2$.

The condenser lens 62 gathers infrared rays emitted by the slit light source 61, and the gathered infrared rays travel through the slit of the slit plate 63 in a slit light beam L. The slit light beam L travels through the aperture stop 64 and the semitransparent mirror 95, and is focused on the cornea C by the projection lens 65.

Figure 5:
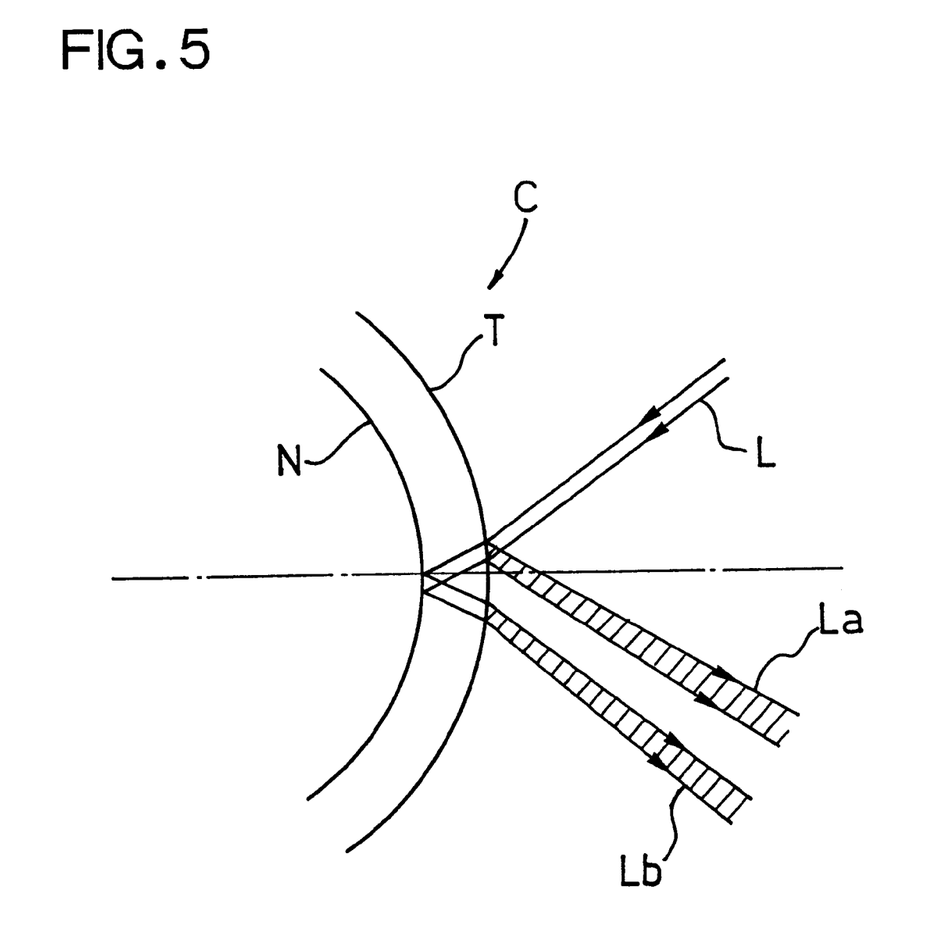
FIG. 5 is a diagrammatic view of assistance in explaining the oblique projection of a light beam through a slit on the cornea by the noncontact tonometer shown in FIG. 1.

Part of the slit light beam L projected on the cornea C is reflected by the corneal surface T, i.e., the boundary between air and the cornea C, part of the slit light beam L penetrated the corneal surface T is reflected by the back corneal surface N as shown in FIG. 5. The intensity of a first reflected light beam La reflected from the corneal surface T is about 100 times as high as that of a second reflected light beam Lb reflected from the back corneal surface N. The slit plate 63 and the back corneal surface N are conjugate with respect to the projection lens 65.

The light receiving optical system 70 has an image forming lens 71 and a linear photosensor 72. The light receiving optical system 70 has the optical axis $O_3$.

Figure 6A:
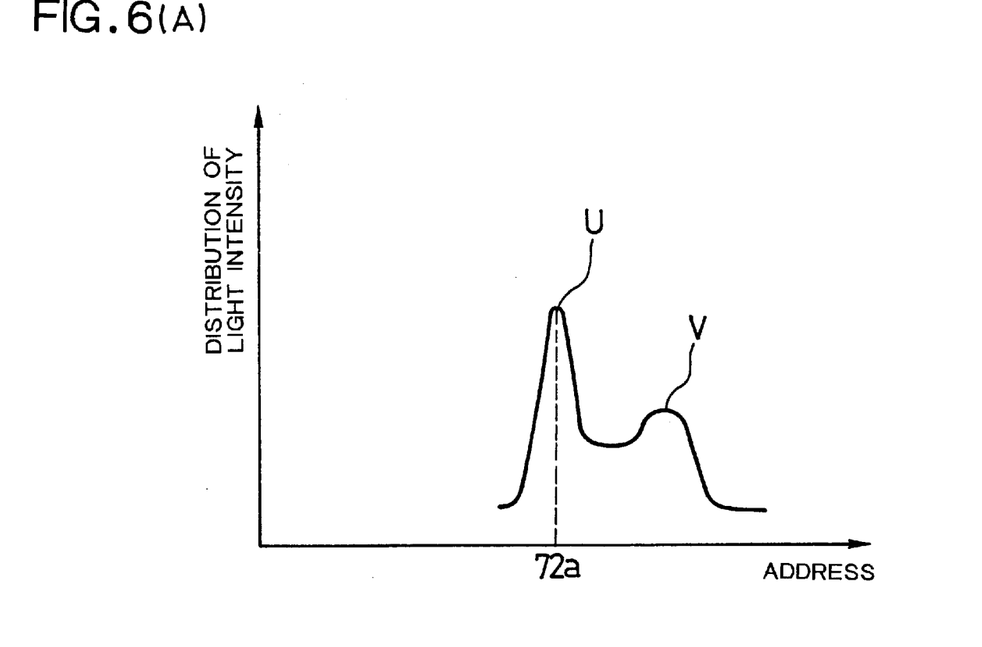
FIG. 6(A) is a graph showing the distribution of light intensity on a linear photosensor included in the noncontact tonometer shown in FIG. 1.
Figure 6B:
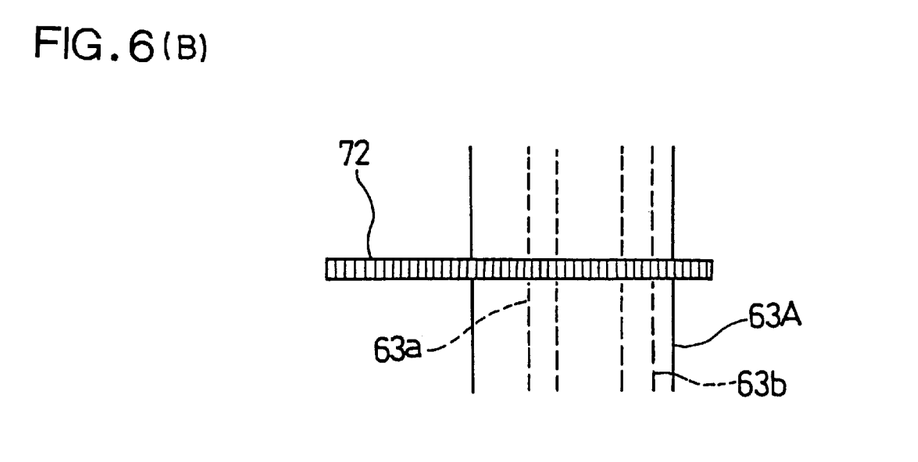
FIG. 6(B) is a view of an image of the slit formed on the linear photosensor.

The first reflected light beam La, i.e., a part of the slit light beam L of the slit projecting optical system 60 reflected from the corneal surface T, and the second reflected light beam Lb, i.e., a part of the slit light beam L of the slit projecting optical system 60 reflected from the back corneal surface N, are focused on the linear photosensor 72 by the image forming lens 71 to form a slit image 63A as shown in FIG. 6(B). FIG. 6(A) shows the distribution of light intensity in the slit image 63A. In FIG. 6(A), a peak U corresponds to the first reflected light beam La reflected by the corneal surface T of the cornea C, and a peak V corresponds to the second reflected light beam Lb reflected from the back corneal surface N of the cornea C. The peak U corresponds to a light image 63a and the peak V corresponds to a light image 63b, of the slit image 63A.

Output signals provided by the light-sensitive elements of the linear photosensor 72 are given to a Z-alignment detecting circuit 73 as shown in FIG. 1.

The index projecting optical system 90 has a Z-alignment light source 91 which emits infrared rays, a condenser lens 92, an aperture stop 93, a pinhole plate 94, a semitransparent mirror 95, and the projection lens 65 disposed on the optical path with its focal point coincided with the pinhole plate 94. The index projecting optical system 90 projects an index light beam W (FIG. 9) wider than the slit light beam L of the slit projecting optical system 60 on the cornea C.

Figure 9:
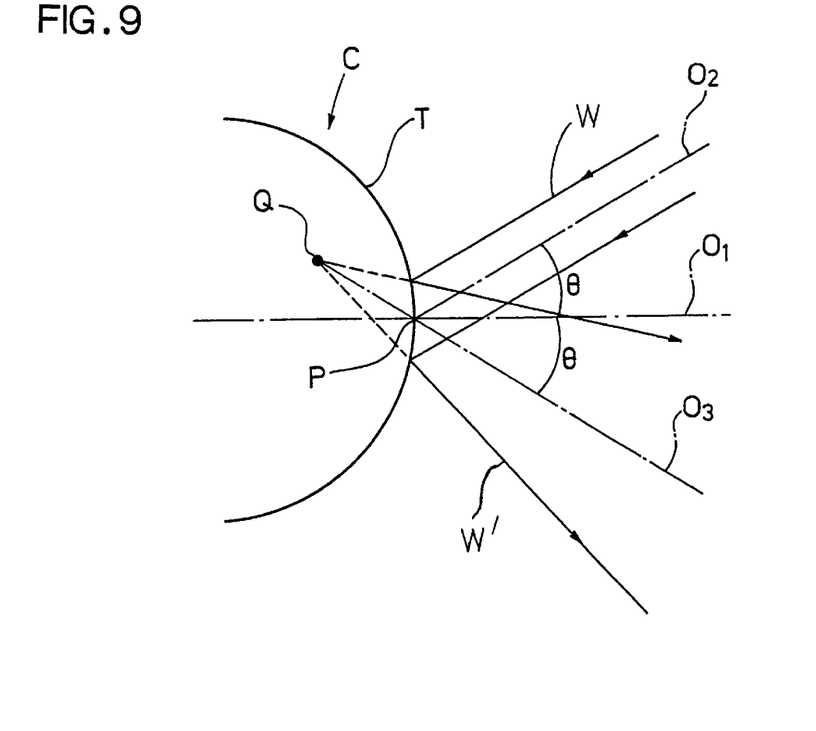
FIG. 9 is a diagrammatic view of assistance in explaining the relation between the cornea and the index light beam in the noncontact tonometer shown in FIG. 1.

Infrared rays emitted by the Z-alignment light source 91 are gathered by the condenser lens 92, the gathered infrared rays travel through the aperture stop 93, and travel through the pin hole of the pinhole plate 94 in the index light beam W. The index light beam W is reflected by the semitransparent mirror 95 and is projected through the projection lens 65 on the cornea C, and the index light beam W is reflected by the corneal surface T so as to form a bright spot image Q as shown in FIG. 9. The aperture stop 93 and the corneal vertex P are conjugate with respect to the projection lens 65.

A reflected index light beam W', i.e., the index light beam W reflected from the corneal surface T, is focused by the image forming lens 71 in a bright spot image Q' on the linear photosensor 72.

Figure 10:
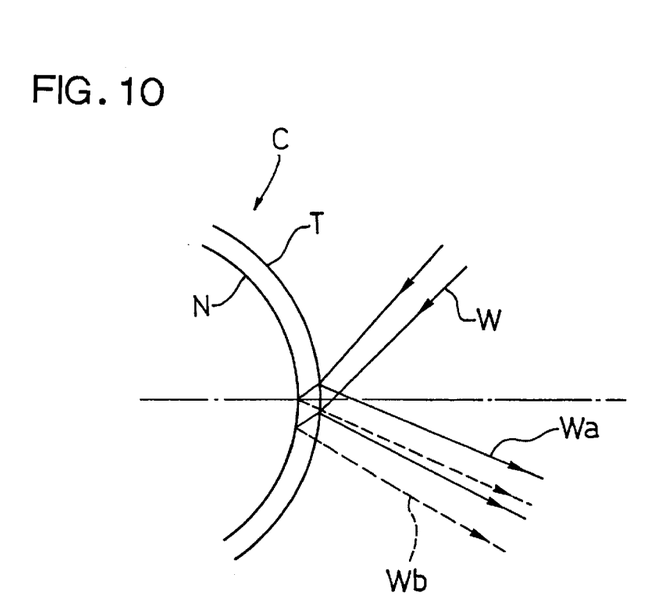
FIG. 10 is a diagrammatic view of assistance in explaining an index light beam projected on the cornea by the noncontact tonometer shown in FIG. 1.
Figure 11:
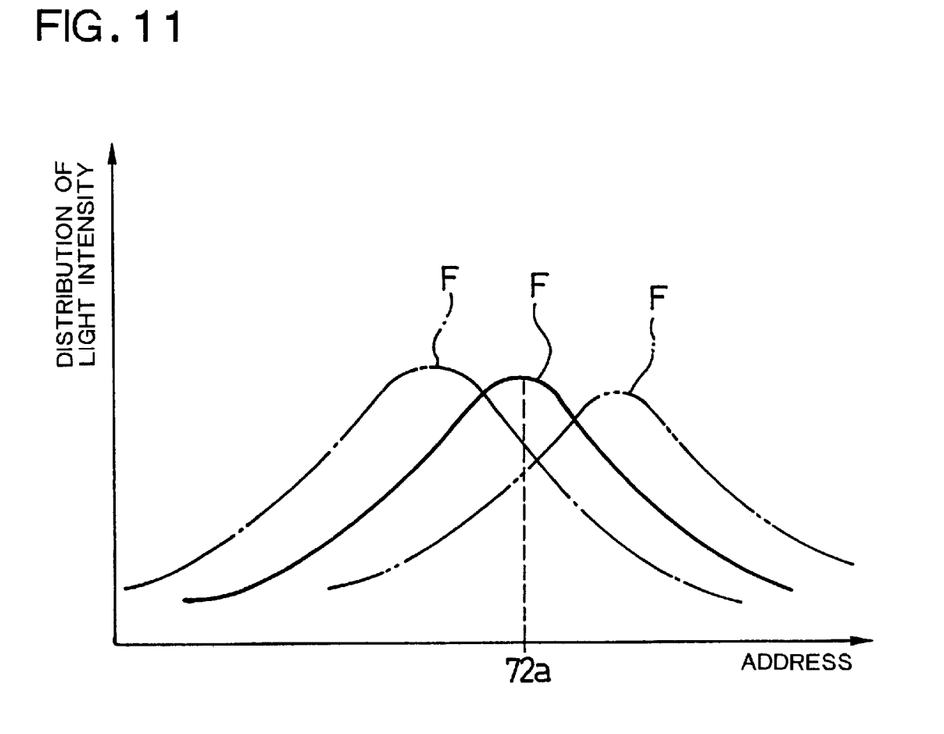
FIG. 11 is a graph showing a light intensity distribution on a linear photosensor when an index light beam is projected on the cornea by the noncontact tonometer shown in FIG. 1.

The width of the index light beam W projected on the cornea C by the index projecting optical system 90 is greater than that of the slit light beam L projected by the slit projecting optical system 60. As shown in FIG. 10, the index light beam W projected on the cornea C is reflected by the corneal surface T in a first reflected index light beam Wa and by the back corneal surface N in a second reflected index light beam Wb. The reflected index light beams Wa and Wb are focused by the image forming lens 71 on the linear photosensor 72 in an aperture image of the aperture stop 93. Since the intensity of the first reflected index light beam Wa is far higher than that of the second reflected index light beam Wb, the aperture image has a light intensity distribution as shown in FIG. 11. In FIG. 11, a peak F corresponds to the light intensity of a central part of an image of the first reflected index light beam Wa on the linear photosensor 72.

When the intraocular pressure measuring unit 115 is designed so that the approximate alignment of the intraocular pressure measuring unit 115 with respect to directions along the Z-axis is completed upon the substantial coincidence of the position of the peak F with a reference position 72a on the linear photosensor 72, the position of the intraocular pressure measuring unit 115 with respect to directions along the Z-axis can be determined on the basis of positional information (location information) about the position of the peak F. The aperture image has a light intensity distribution indicated by a chain curve in FIG. 11 when the intraocular pressure measuring unit 115 is excessively close to the cornea C, and has a light intensity distribution indicated by a two-dot chain curve in FIG. 11 when the intraocular pressure measuring unit 115 is excessively apart from the cornea C.

Since the index light beam W is wide and hence the first reflected index light beam Wa is wide, the linear photosensor 72 is able to receive the first reflected index light beam Wa even if the intraocular pressure measuring unit 115 is dislocated greatly in a direction along the Z-axis from an appropriate position.

The Z-alignment detecting circuit 73 determines positional information (location information) about the peaks U and V shown in FIGS. 6(A) and the peak F shown in FIG. 11, and gives the positional information to the control circuit 80 and the corneal thickness measuring circuit 74. The corneal thickness measuring circuit 74 calculates the thickness of the cornea C on the basis of the positional information about the peaks U and V by a known means. The control circuit 80 controls a motor 112 on the basis of the positional information abut the peaks U and V to move the intraocular pressure measuring unit 115 along the Z-axis to position the intraocular pressure measuring unit 115 correctly with respect to directions along the Z-axis for Z-alignment.

Referring to FIG. 7 showing the noncontact tonometer in a side elevation, a table 101 is mounted on a base 100 internally provided with a power supply. The table 101 can be moved in an XY plane by operating a control lever 102. The control lever 102 is provided with a manually operated switch 103, which is operated in a manual mode. The noncontact tonometer in this embodiment is operated in a manual control mode. A motor 104 and a column 105 are set on the table 101. The column 105 is moved in vertical directions along the Y-axis through a rack-and-pinion mechanism by the motor 104. A table 106 is supported on the column 105.

Figure 8:
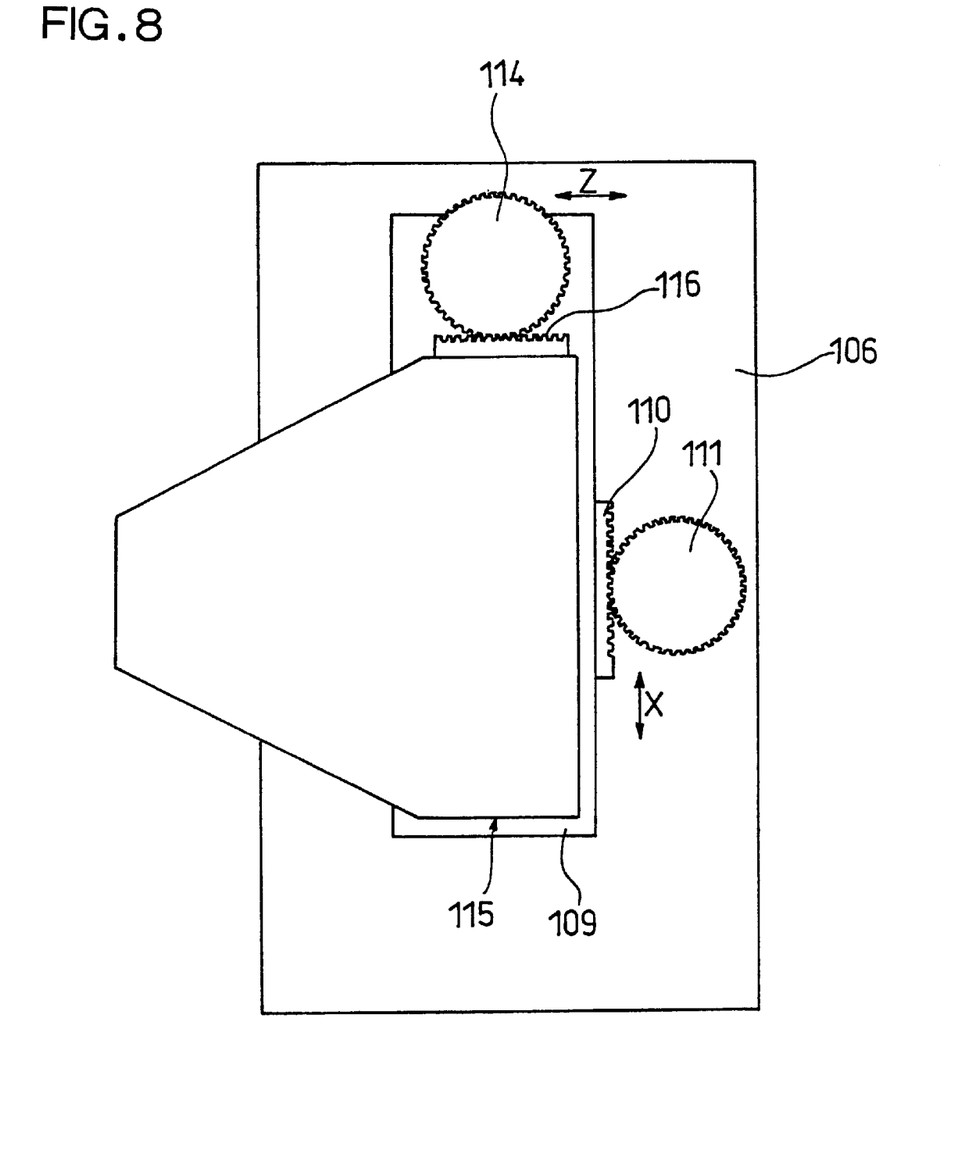
FIG. 8 is a plan view of an essential part of the noncontact tonometer shown in FIG. 1.

A motor 108 is mounted on the table 106, and a column 107 is set up on the table 106. A table 109 is supported for sliding movement on the column 107. As shown in FIG. 8, a rack 110 is attached to the back side of the table 109. A pinion 111 mounted on the output shaft of the motor 108 and the rack 110 are engaged. A motor 112 is mounted on the table 109 and a column 113 is set up on the table 109. A pinion 114 is mounted on the output shaft of the motor 112. The intraocular pressure measuring unit 115 is supported for sliding movement on the column 113. A rack 116 attached to a side of the intraocular pressure measuring unit 115, and the pinion 114 are engaged. The intraocular pressure measuring unit 115 is provided internally with the optical systems shown in FIGS. 1 and 2.

The motors 104, 108 and 112 are controlled by control signals provided by the control circuit 80. The intraocular pressure measuring unit 115 is driven for movement along the Y-axis, the X-axis and the Z-axis by control signals given to the motors 104, 108 and 112, respectively, for the automatic alignment of the intraocular pressure measuring unit 115.

The operation of the noncontact tonometer will be described hereinafter.

The fixation target light source 31 of the fixation target projecting optical system 30 is turned on for the fixation of the subject's eye E, and the Z-alignment light source 91 of the index projecting optical system 90 is turned on. The examiner observes an anterior segment image E' of the anterior segment of the eye E displayed on the screen G of the monitor by the anterior segment observation optical system 10 and makes the rough alignment of the intraocular pressure measuring unit 115. The XY-alignment detecting circuit 42 and the Z-alignment detecting circuit 73 calculate the position of the intraocular pressure measuring unit 115 (alignment position) relative to the cornea C on the basis of the output (alignment positional information) provided by the photosensor 41 of the XY-alignment detecting optical system 40 and the output (alignment positional information) provided by the linear photosensor 72 of the light receiving optical system 70, and displays the calculated position on the screen (informing means) G of the monitor for the examiner. The light source 61 of the slit projecting optical system 60 is not yet turned on.

The position of the intraocular pressure measuring unit 115 with respect to directions along the Z-axis is adjusted on the basis of the positional information on the peak F shown in FIG. 11 provided by the Z-alignment detecting circuit 73. Since the first reflected index light beam Wa is wide, the linear photosensor 72 is able to receive the first reflected index light beam Wa even if the intraocular pressure measuring unit 115 is dislocated greatly with respect to directions along the Z-axis. Therefore, the amount and the direction of dislocation of the intraocular pressure measuring unit 115 from the correct position can be known, a direction along the Z-axis in which the intraocular pressure measuring unit 115 is to be moved, and a position to which the intraocular pressure measuring unit 115 is moved can be displayed on the screen G, so that the intraocular pressure measuring unit 115 can quickly be moved in an appropriate direction.

The examiner moves the table 101 consulting the information displayed on the screen G, and the control circuit 80 drives the motors 104, 108 and 112 to position the intraocular pressure measuring unit 115 correctly. The movement of the table 101 can be known from the variation of the output of the linear photosensor 72, i.e., the variation of the output of the Z-alignment detecting circuit 73.

When the intraocular pressure measuring unit 115 is aligned correctly relative to the cornea C by driving the motors 104, 108 and 112 by the control circuit 80, the bright spot image R'2 is located inside the auxiliary alignment mark H on the screen G of the monitor. The Z-alignment light source 91 of the index projecting optical system 90 is turned off and the light source 61 of the slit projecting optical system 60 is turned on when the bright spot image R'2 is moved to the center of the auxiliary alignment mark H and the peak F shown in FIG. 11 is located near the reference position 72*a* on the linear photosensor 72.

The Z-alignment detecting circuit 73 calculates the position on the Z-axis of the intraocular pressure measuring unit 115 on the basis of the output of the linear photosensor 72 provided when the peak F shown in FIG. 11 is located near the reference position 72*a* on the linear photosensor 72 immediately before the Z-alignment light source 91 is turned off. The control circuit 80 controls the motor 112 on the basis of the calculated position on the Z-axis of the intraocular pressure measuring unit 115 to move the intraocular pressure measuring unit 115 along the Z-axis.

When the light source 61 of the slit projecting optical system 60 is turned on, the slit image 63A as shown in FIG. 6(B) is formed on the linear photosensor 72. The position of the intraocular pressure measuring unit 115 on the Z-axis is adjusted for Z-axis alignment on the basis of a light intensity distribution in the slit image 63A; that is, the intraocular pressure measuring unit 115 is moved to make the peak U shown in FIG. 6(A) coincide with the reference position 72*a* on the linear photosensor 72. Upon the coincidence of the peak U with the reference position 72*a* on the linear photosensor 72, i.e., upon the completion of Z-axis alignment, the corneal thickness measuring circuit 74 calculates the thickness of the cornea C by processing positional information on the positions of the peaks U and V provided by the Z-alignment detecting circuit 73 on the basis of the output (alignment positional information) of the linear photosensor 72.

Positional information provided by the XY-alignment detecting circuit 42 (positional information based on a position detecting signal provided by the XY-alignment detecting circuit 42) when the Z-alignment detecting circuit 73 provides the information for the calculation of the thickness of the cornea C is stored in a storage unit (storage means) included in the control circuit 80. An arithmetic unit, not shown, included in the control circuit 80 makes the puffing nozzle 12 puff an air pulse to flatten the cornea C when the positional information (alignment positional information) provided by the XY-alignment detecting circuit 42 and stored in the storage unit does not change. The amount of deformation is measured by the cornea deformation detecting optical system 50.

Suppose that the positional information provided by the XY-alignment detecting circuit 42 and indicating the position of the intraocular pressure measuring unit 115 when the thickness of the cornea C is measured is measuring position information, and the positional information provided by the XY-alignment detecting circuit 42 for puffing an air pulse immediately after the measurement of the thickness of the cornea C is puffing position information. Then, a fact that the positional information provided by the XY-alignment detecting circuit 42 does not change signifies that the puffing position indicated by the puffing position information is dislocated scarcely from the measuring position indicated by the measuring position information, i.e., the measured thickness of the cornea C is in an allowable range and can be used for the correction of the measured intraocular pressure.

The arithmetic unit (not shown) of the control circuit 80 calculates an intraocular pressure on the basis of the amount of deformation of the cornea C detected by the cornea deformation detecting optical system 50 and the pressure of the air pulse puffed by the puffing nozzle 12, and corrects the calculated intraocular pressure on the basis of the thickness of the cornea C. Data representing the relation between true intraocular pressure determined by direct measurement and corneal thickness, and data representing the relation between the same data and intraocular pressure measured by flattening the cornea C are stored beforehand in the storage unit of the control circuit 80. These data stored in the storage unit are used for the correction of the calculated intraocular pressure by the thickness of the cornea C.

If the stored positional information provided by the XY-alignment detecting circuit 42 varies due to the small involuntary movement of the eye E, the control circuit 80 controls the motors 104, 108 and 112 again according to the output signals of the XY-alignment detecting circuit 42 and the Z-alignment detecting circuit 73 to readjust the position of the intraocular pressure measuring unit 115 relative to the cornea C, and then the corneal thickness measuring circuit 74 calculates the thickness of the cornea C. If the information provided by the XY-alignment detecting circuit 42 and stored in the storage unit does not change, the control circuit 80 makes the puffing nozzle 12 puff an air pulse to flatten the cornea C. Then, the arithmetic unit of the control circuit 80 calculates an intraocular pressure on the basis of a detected amount of deformation of the cornea C and the pressure of the air pulse puffed by the puffing nozzle 12, and corrects the calculated intraocular pressure on the basis of the thickness of the cornea C.

The thickness of the cornea C, the calculated intraocular pressure and the corrected intraocular pressure are displayed on the screen G of the monitor.

A puffing means, not shown, puffs an air pulse through the puffing nozzle 12, and the pressure of the air pulse is measured by a pressure sensor (not shown) included in the puffing means.

When the eye E makes small involuntary movement frequently and intraocular pressure measurement cannot be started after the repetition of a corneal thickness measuring operation by a predetermined number of cycles, the control circuit 80 makes the puffing nozzle 12 puff an air pulse for intraocular pressure measurement even if the stored information provided by the XY-alignment detecting circuit 4 varies. In such a case, the examiner is informed that a section of the cornea C where the corneal thickness was measured and a section of the cornea C at which the air pulse was puffed are different by displaying information to effect on the screen G of the monitor.

The position of the intraocular pressure measuring unit 115 may be readjusted by controlling the motors 104, 108 and 112 by the control circuit 80 with reference to measured position indicated by the measured positional information, and intraocular pressure measurement may be executed.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A noncontact tonometer which measures intraocular pressure of a subject's eye after measuring the thickness of the cornea of the eye, said noncontact tonometer comprising:

a position detecting means for detecting the position of the noncontact tonometer relative to the cornea by projecting a light beam on the cornea and detecting the reflected light beam reflected from the cornea;

a corneal thickness measuring means for measuring the thickness of the cornea by projecting a light beam on the cornea and detecting the reflected light beam reflected from the cornea;

a storage means for storing positional information provided by the position detecting means when the thickness of the cornea is measured by the corneal thickness measuring means;

an intraocular pressure measuring means for measuring the intraocular pressure of the eye by applying an air pulse to the cornea and optically detecting an amount of deformation of the cornea;

a comparing means for comparing the positional information provided by the position detecting means and the positional information stored in the storage means after the measurement of the thickness of the cornea by the corneal thickness measuring means; and a control means for controlling an operation for applying an air pulse to the cornea by deciding on the basis of information provided by the comparing means and representing the result of comparison whether or not intraocular pressure measurement is to be executed following corneal thickness measurement.

2. The noncontact tonometer according to claim 1, wherein the control means does not execute an operation to start intraocular pressure measurement if it is known from the information provided by the comparing means that the difference between the positional information provided by the position detecting means and the positional information stored in the storage means exceeds a predetermined value, and executes an operation to perform corneal thickness measurement again.

3. The noncontact tonometer according to claim 1, wherein the control means corrects the measured intraocular pressure on the basis of a corneal thickness calculated by corneal thickness measurement.

4. The noncontact tonometer according to claim 1 further comprising an informing means for informing the examiner of the calculated corneal thickness, the intraocular pressure or the corrected intraocular pressure.

* * * * *